(12) United States Patent
Tsuji et al.

(10) Patent No.: US 6,747,017 B2
(45) Date of Patent: *Jun. 8, 2004

(54) METHOD OF INHIBITING HAIR GROWTH

(75) Inventors: Naoko Tsuji, Tochigi (JP); Shigeru Moriwaki, Tochigi (JP); Atsushi Ohuchi, Tochigi (JP); Yoshinori Takema, Tochigi (JP); Yasuto Suzuki, Tochigi (JP); Genji Imokawa, Tochigi (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/220,691

(22) Filed: Dec. 28, 1998

(65) Prior Publication Data

US 2002/0037880 A1 Mar. 28, 2002

(30) Foreign Application Priority Data

Jan. 14, 1998 (JP) .......................... 10-005959

(51) Int. Cl.[7] ........................ A01N 57/26; A61K 31/66; A61K 31/095
(52) U.S. Cl. ...................... 514/137; 514/114; 514/143; 514/706
(58) Field of Search ........................... 514/80, 114, 137, 514/143, 706

(56) References Cited

U.S. PATENT DOCUMENTS

| | | | |
|---|---|---|---|
| 4,327,111 A | * | 4/1982 | Sundeen et al. ............ 514/467 |
| 4,513,009 A | | 4/1985 | Roques et al. |
| 4,720,489 A | | 1/1988 | Shander |
| 4,720,789 A | | 1/1988 | Hector et al. |
| 5,095,007 A | | 3/1992 | Ahluwalia |
| 5,096,911 A | | 3/1992 | Ahluwalia et al. |
| 5,132,293 A | | 7/1992 | Shander et al. |
| 5,143,925 A | * | 9/1992 | Shander et al. ............ 514/378 |
| 5,155,100 A | * | 10/1992 | Erion et al. ................ 514/119 |
| 5,330,978 A | * | 7/1994 | Wakimasu et al. ......... 514/118 |
| 5,364,885 A | | 11/1994 | Ahluwalia et al. |
| 5,378,455 A | * | 1/1995 | Kealey et al. ............... 424/73 |
| 5,411,991 A | | 5/1995 | Shander et al. |
| 5,444,090 A | * | 8/1995 | Ahluwalia .................. 514/547 |
| 5,455,234 A | * | 10/1995 | Ahluwalia et al. ........... 514/46 |
| 5,468,476 A | * | 11/1995 | Ahluwalia et al. ........... 424/73 |
| 5,474,763 A | * | 12/1995 | Shander et al. ............. 424/73 |
| 5,554,608 A | | 9/1996 | Ahluwalia et al. |
| 5,648,394 A | | 7/1997 | Boxall et al. |
| 5,652,227 A | * | 7/1997 | Teronen et al. .............. 514/75 |
| 5,652,262 A | * | 7/1997 | Crimmin et al. ............ 514/507 |
| 5,652,273 A | | 7/1997 | Henry et al. |
| 5,674,477 A | | 10/1997 | Ahluwalia |
| 5,728,736 A | * | 3/1998 | Shander et al. ............ 514/561 |
| 5,776,442 A | | 7/1998 | Ahluwalia |
| 5,824,665 A | | 10/1998 | Henry et al. |
| 5,837,224 A | * | 11/1998 | Voorhees et al. ............ 424/59 |
| 5,840,752 A | * | 11/1998 | Henry et al. ................ 514/460 |
| 5,908,867 A | | 6/1999 | Henry et al. |
| 5,939,458 A | | 8/1999 | Henry et al. |
| 5,958,946 A | | 9/1999 | Styczynski et al. |
| 5,962,466 A | * | 10/1999 | Styczynski et al. ......... 514/292 |
| 6,020,006 A | | 2/2000 | Styczynski et al. |
| 6,037,326 A | | 3/2000 | Styczynski et al. |
| 6,060,471 A | | 5/2000 | Styczynski et al. |
| 6,075,052 A | | 6/2000 | Suzuki et al. |
| 6,093,748 A | | 7/2000 | Ahluwalia et al. |
| 6,096,730 A | * | 8/2000 | Collins et al. ............. 514/107 |
| 6,121,269 A | | 9/2000 | Henry et al. |
| 6,171,595 B1 | | 1/2001 | Suzuki et al. |
| 6,218,435 B1 | | 4/2001 | Henry et al. |
| 6,235,737 B1 | | 5/2001 | Styczynski et al. |
| 6,239,170 B1 | | 5/2001 | Ahluwalia et al. |
| 6,248,751 B1 | | 6/2001 | Ahluwalia et al. |
| 6,299,865 B1 | | 10/2001 | Styczynski et al. |
| 6,375,948 B1 | * | 4/2002 | Tsuji et al. ................ 424/70.1 |

FOREIGN PATENT DOCUMENTS

| | | | | |
|---|---|---|---|---|
| EP | 166377 | * | 1/1986 | |
| EP | 0 532 219 | | 3/1993 | |
| FR | 2485927 | * | 1/1982 | |
| JP | 60-181007 | | 9/1985 | |
| JP | 5-105698 | | 4/1993 | |
| JP | 8-133936 | | 5/1996 | |
| JP | 8157448 | | 6/1996 | |
| JP | 10265359 | * | 10/1998 | |
| JP | 2969451 B1 | * | 11/1999 | ............ A61K/7/00 |
| WO | WO 9115507 A1 | * | 10/1991 | .......... A61K/37/64 |
| WO | WO 92/03140 | | 3/1992 | |
| WO | WO 94/10967 | | 5/1994 | |
| WO | WO 95/07924 | | 3/1995 | |
| WO | 9719102 | * | 5/1997 | |
| WO | WO 98/25580 | | 6/1998 | |
| WO | WO 9825580 A1 | * | 6/1998 | ............ A61K/7/06 |

OTHER PUBLICATIONS

Z. P. Kortylewicz, et al., Journal of Medicinal Chemistry, vol. 33, No. 1, pp. 263–273, "Phosphoramidate Peptide Inhibitors of Human Skin Fibroblast Collagenase", 1990.

(List continued on next page.)

Primary Examiner—Jon P. Weber
(74) Attorney, Agent, or Firm—Oblon, Spivak, McClelland, Maier & Neustadt, P.C.

(57) ABSTRACT

Disclosed herein are a method of inhibiting hair growth, which comprises administering an inhibitor of elastase-like enzymes or a neutral endopeptidase inhibitor, and use of an inhibitor of elastase-like enzymes or a neutral endopeptidase inhibitor for the preparation of a hair-growth inhibitor.

4 Claims, 1 Drawing Sheet

OTHER PUBLICATIONS

Journal of Dermatological Science 7 (1994) 202–209,Ralf Paus, Niels Krejci–Papa, Lingna Li, Beate M. Czarnetzki, Robert M. Hoffman.

Stuart H. Yuspa, et al.; *Regulation of Hair Follicle Development: An In Vitro Model for Hair Follicle Invasion of Dermis and Associated Connective Tissue Remodeling;* The Journal of Investigative Dermatology; Tissue Remodeling in HP Development; vol. 101. No. 1 Supplemental, p. 27S–32S; Jul. 1993.

Ralf Paus; *Correlation of Proteolytic Activities of Organ Cultured Intact Mouse Skin with Defined Hair Cycle Stages;* Journal of Dermatological Science; Journal of Dermatological Science 7 (1994) 202–209.

JJ Reynolds; *Collagenases and Tissue Inhibitors of Metalloproteinases: A Functional Balance in Tissue Degradation,* Oral Diseases (1996) 2, pp. 70–76.

R.D. Sinclair, et al.; *Handbook of Diseases of the Hair and Scalp;* pp. 7–10; Blackwell Science Ltd. (1999).

Anita E. Yu, et al.; *Matrix Metalloproteinases Novel Targets for Directed Cancer Therapy,* Drugs & Aging 1997 Sep. 11 (3); pp. 229–244.

Thomas T. Kawabe, et al., *Location of TIMP in Cycling Mouse Hair;* Development 111, pp. 877–879 (1991).

\* cited by examiner

METHOD OF INHIBITING HAIR GROWTH

BACKGROUND OF THE INVENTION

1. Field of the Invention

The present invention relates to a method of inhibiting hair growth, and more particularly to a method of inhibiting hair growth, by which hair growth on the legs and arms, and the like can be effectively inhibited, and use of a specific enzyme inhibitor for the preparation of a hair-growth inhibitor.

2. Description of the Background Art

A biological function of the scalp hair and body hair is to protect important organs of the head, chest, limbs and the like. With the development of clothes and protecting means, however, the organ-protecting function carried by the body hair has come to be unimportant.

The scalp hair is generally desired to be thick. In recent years, however, the tendency to prefer having no hair on, particularly, limbs and the like has been strengthened from the viewpoint of an aesthetic appearance. Therefore, various methods for removing the body hair have been developed and used. Specific examples thereof include mechanical removing methods making use of a shaver, hair plucker or the like, methods of using a depilatory to depilate body hair out of its root, methods of using a hair remover to remove body hair by its chemical reaction, etc.

However, these methods for removing the body hair are accompanied by the physical or chemical irritation of the skin, and the lastingness of their removing effects on the body hair is limited even though there is some difference between the methods. Therefore, such a treatment for removing the body hair must be conducted again after a certain period of time. It is thus desired to lighten the removal treatment of the body hair.

International Application WO98/25580 published Jun. 18, 1998 discloses a method for reducing hair growth by inhibiting the activity of a matrix metalloproteinase in the skin. The present invention intends the same purpose, i.e., providing a method of inhibiting hair growth. However, the researchers of the present invention found that hair growth is deeply influenced by the activity of elastase-like enzymes. Thus, there is fundamental difference in the present invention from the prior art, which provides a novel method characterized by inhibition of the activity of elastase-like enzymes.

SUMMARY OF THE INVENTION

Accordingly, it is an object of the present invention to provide a method of inhibiting hair growth, by which the growth of body hair can be effectively inhibited to reduce the number of removal treatments of the body hair.

In view of the foregoing circumstances, the present inventors have carried out an extensive investigation. As a result, it has been quite surprisingly found that inhibitors of elastase-like enzymes which digest elastin known as a structural protein in the artery, tendon, skin or the like, and inhibitors of neutral endopeptidases that are enzymes which digest opioid peptides such as enkephalin, and neuropeptides such as substance P and bradykinin have an excellent inhibitory effect on hair growth, thus leading to completion of the present invention.

According to the present invention, there is thus provided a method of inhibiting hair growth, which comprises administering an inhibitor of elastase-like enzymes or a neutral endopeptidase inhibitor.

According to the present invention, there is also provided use of an inhibitor of elastase-like enzymes or a neutral endopeptidase inhibitor for the preparation of a hair-growth inhibitor.

According to the present invention, an excellent inhibitory effect on hair growth can be achieved, and hair-growth inhibitors high in safety for the human body can also be provided.

DETAILED DESCRIPTION OF THE PREFERRED EMBODIMENTS

Figure 1:
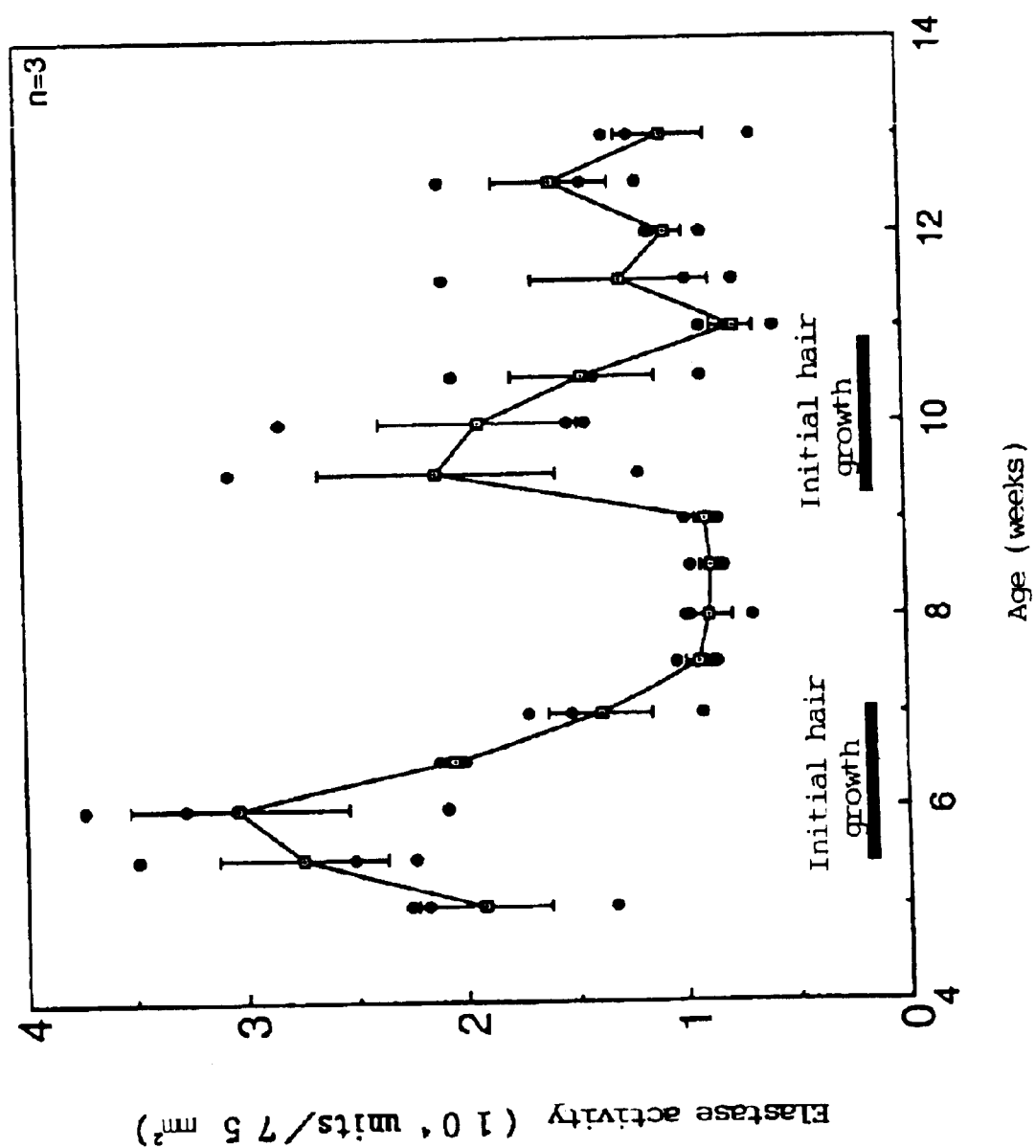
FIG. 1 diagrammatically illustrates the relationship between a hair cycle and the activity of an elastase in cutaneous tissue.

As the inhibitor of elastase-like enzymes useful in the practice of the present invention, is preferred an elastase inhibitor, particularly, an inhibitor of elastase-like enzymes derived from a dermoepidermal fibroblast. Such inhibitors include substances which exhibit an inhibitory activity of at least 50% at 1 mM in an enzyme activity-measuring system making use of an enzyme solution extracted from, for example, cultured human fibroblasts with a 0.1% Triton X-100/0.2 M Tris-hydrochloric acid buffer solution (pH: 8.0) and containing N-succinyl-Ala-Ala-Ala-p-nitroanilide as a substrate.

As the neutral endopeptidase inhibitor useful in the practice of the present invention, is preferred an inhibitor of a neutral endopeptidase derived from a dermoepidermal fibroblast. Such inhibitors include substances which exhibit an inhibitory activity of at least 50% at 1 mM in an enzyme activity-measuring system making use of an enzyme solution extracted from, for example, cultured human fibroblasts with a 0.1% Triton X-100/0.2 M Tris-hydrochloric acid buffer solution (pH: 8.0) and containing glutaryl-Ala-Ala-Phe-4-methoxy-2-naphthylamine as a substrate in an MES (2-morpholino-ethane sulfonic acid) buffer solution (100 mM, pH: 6.5) to which sodium chloride (300 mM) has been added.

Examples of such elastase-like enzyme inhibitors or neutral endopeptidase inhibitors include phosphonic acid derivatives, mercaptopropionamide derivatives and salts thereof.

The phosphonic acid derivatives include compounds represented by the following general formula (1):

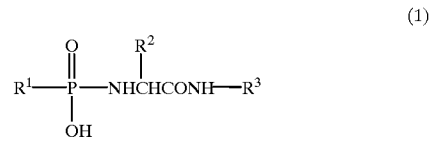

(1)

wherein $R^1$ is a hydrogen atom, a hydroxyl group, a hydrocarbon group which may be substituted, or a sugar residue which may be substituted, $R^2$ is a hydrogen atom, a hydrocarbon group which may be substituted, or a sugar residue which may be substituted, and is a hydrogen atom or a —CH($R^4$)COOH (in which $R^4$ is a hydrogen atom or a hydrocarbon group which may be substituted), and salts thereof.

In the formula (1), the hydrocarbon groups which are represented by $R^1$, $R^2$ and $R^4$ and may be substituted may be either saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. These hydrocarbon groups preferably have 1 to 24 carbon atoms, particularly 1 to 18 carbon atoms.

Of the hydrocarbon groups represented by $R^1$, $R^2$ and $R^4$, the alkyl, cyclic alkyl, aromatic hydrocarbon and aralkyl groups are preferred. The alkyl groups are preferably linear or branched alkyl groups having 1 to 12 carbon atoms, with n-propyl, isopropyl, n-butyl, isobutyl, tert-butyl and isoamyl groups being more preferred. The cyclic alkyl groups are preferably 5- to 7-membered alicyclic alkyl groups, with cyclopentyl and cyclohexyl group being more preferred. The aromatic hydrocarbon groups are preferably aromatic hydrocarbon groups having 6 to 14 carbon atoms, such as phenyl and naphthyl groups. The aralkyl groups are preferably alkyl groups having 1 to 5 carbon atoms, which have been substituted by an aromatic hydrocarbon group having 6 to 12 carbon atoms, and examples thereof include 2-phenylethyl (=phenethyl), 2-(1-naphthyl)ethyl and 2-(2-naphthyl)ethyl groups.

Examples of atoms or groups which may be substituted on the hydrocarbon groups represented by $R^1$, $R^2$ and $R^4$ include halogen atoms, a hydroxyl group, alkoxyl groups, acyl groups, an amino group which may be protected, and heterocyclic groups. The halogen atoms include chlorine, bromine and iodine atoms. The alkoxyl groups are preferably alkoxyl groups having 1 to 12 carbon atoms, and examples thereof include methoxy, ethoxy and isopropoxy groups. The acyl groups are preferably alkanoyl groups having 1 to 12 carbon atoms, and examples thereof include acetyl, propionyl and butyryl groups. Examples of the amino group which may be protected include amino, $C_{1-8}$-acylamino and $C_{1-6}$-alkylamino di-($C_{1-6}$-alkyl)amino groups. The heterocyclic groups are preferably 5- to 14-membered monocyclic or fused ring groups having, as heteroatom(s), 1 to 3 nitrogen, oxygen and/or sulfur atoms, and examples thereof include pyridyl, pyridazinyl, furyl, thienyl, indolyl, thiazolyl, imidazolyl, benzofuryl and benzothienyl groups.

The sugar residues include monosaccharide residues and oligosaccharide residues. Examples of groups which may be substituted on these sugar residues include alkyl, acyl and aralkyl groups. Examples of the alkyl, acyl and aralkyl groups include the same $C_{1-12}$ alkyl, $C_{1-6}$ acyl and $C_{6-12}$-aryl-$C_{1-6}$-alkyl groups as mentioned above.

These phosphonic acid derivatives can be prepared in accordance with, for example, the process described in Japanese Patent Application Laid-Open No. 105698/1993.

The mercaptopropionamide derivatives include, for examples, compounds represented by the following general formula (2):

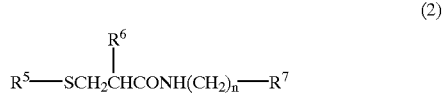

(2)

wherein $R^5$ is a hydrogen atom or an acyl group, $R^6$ is a hydrogen atom or a hydrocarbon group which may be substituted, $R^7$ is a hydrogen atom, a carboxyl group, an alkoxycarbonyl group, a hydrocarbon group which may be substituted, a heterocyclic group which may be substituted, or an acyl group, and n is a number of 1 to 20.

In the formula (2), the acyl groups represented by $R^5$ and $R^7$ include alkanoyl groups and arylcarbonyl groups. The alkanoyl groups are preferably alkanoyl groups having 1 to 12 carbon atoms, and examples thereof include acetyl, propionyl and butyryl groups. The arylcarbonyl groups are preferably having 7 to 15 carbon atoms, and examples thereof include benzoyl, substituted benzoyl, naphthylcarbonyl and substituted naphthylcarbonyl groups. Examples of groups or atoms substituted on the benzoyl and naphthylcarbonyl groups include $C_{1-6}$ alkyl groups, $C_{1-6}$ alkoxyl groups, halogen atoms, an amino group, a hydroxyl group and $C_{1-6}$ alkanoyloxy groups. n is preferably 1 to 6, more preferably 1 or 2.

The hydrocarbon groups which are represented by $R^6$ and $R^7$ and may be substituted include the same groups as those mentioned above as to $R^1$, $R^2$ and $R^4$.

The heterocyclic group represented by $R^7$ is preferably a 5- to 14-membered monocyclic or fused ring group having, as heteroatom(s), 1 to 3 nitrogen, oxygen and/or sulfur atoms, and examples thereof include pyridyl, pyridazinyl, furyl, thienyl, indolyl, thiazolyl, imidazolyl, benzofuryl, benzothienyl, pyrrolidinyl, piperidinyl, morpholinyl and piperazinyl groups. Examples of atoms or groups which may be substituted on the heterocyclic group include halogen atoms, a hydroxyl group, alkoxyl groups, acyl groups and an amino group which may be protected. Specific examples of these substituents include the same substituents as the substituents of the hydrocarbon groups mentioned above as to $R^1$, $R^2$ and $R^4$.

The alkoxycarbonyl group represented by $R^7$ includes alkoxycarbonyl groups the alkoxy moiety of which has 1 to 12 carbon atoms, and specific examples thereof include methoxycarbonyl, ethoxycarbonyl, isopropoxycarbonyl and butoxycarbonyl groups.

These mercaptopropionamide derivatives can be prepared in accordance with, for example, the process described in Japanese Patent Application Laid-Open No. 24354/1982. Incidentally, these mercaptopropionamide derivatives are known to have an inhibitory effect on mammalian collagenases, but not known at all to have an inhibitory effect on elastase-like enzymes.

The phosphonic acid derivatives and mercaptopropionamide derivatives may be used in the form of pharmaceutically acceptable salts or hydrates. Examples of the salts include alkali metal salts, alkaline earth metal salts, organic amine salts and amino acid salts. Examples of the alkali metal salts include the sodium salt and potassium salt. The examples of the alkaline earth metal salts include the calcium salt and magnesium salt. Examples of the organic amine salts include the ammonium salts, methylamine salt, triethylamine salt and pyridinium salt. Examples of the amino acid salts include the arginine salt, lysine salt and histidine salt. The alkali metal salts and amino acid salts are more preferred. As sites at which a salt is formed, may be mentioned the moieties of the phosphonic acid residue and carboxyl group in the phosphonic acid derivatives and the moieties of the thiol group and carboxyl group in the mercaptopropionamide derivatives. In the case where a salt is formed, the salt may be formed at both or one of these residues.

No particular limitation is imposed on the hair-growth inhibitor useful in the practice of the present invention. However, it is preferably used in the form of an external skin-care composition, particularly, a cosmetic composition related to hair removal, depilation or shaving. Specific examples of such a cosmetic composition include hair removers in the form of paste, cream or aerosol, depilatories in the form of wax, gel or sheet, after-treatment compositions used for a treatment after hair removal or depilation, such as lotion and cream, antiperspirant and deodorant cosmetics such as deodorant lotion, deodorant powder, deodorant spray and deodorant stick, treatment compositions before shaving, such as pre-shave lotion, shaving compositions such as shaving cream, and treatment compositions after shaving, such as after-shave lotion.

It is preferred that the amount of the active ingredient incorporated into the hair-growth inhibitor according to the present invention be generally 0.0001 to 10% by weight, particularly, 0.001 to 3% by weight based on the total weight of the inhibitor from the viewpoints of the inhibitory effect on hair growth, profitability, etc.

In the hair-growth inhibitor according to the present invention, various optional ingredients commonly used for cosmetics, quasi-drugs and drugs may be suitably incorporated as needed so far as no detrimental influence is thereby imposed on the effects of the present invention. Examples of such optional ingredients include purified water, ethanol, oily substances, moisturizers, thickeners, preservatives, emulsifiers, medicinally-effective agents, powders, ultraviolet absorbents, pigments, perfume bases and emulsion stabilizers.

EXAMPLE 1

[Hair Cycle and Elastase Activity]

After a fascia was removed from the shaved back skin of each of SD rats (male) aged 5 weeks to 13 weeks that were in various hair-growing stages, cutaneous tissue specimens 4 mm in diameter were prepared. A phosphate buffer solution (PBS) was then put in a peripheral part of a Petri dish for organ culture (Falcon 3037) for the purpose of keeping humidity constant, and the cutaneous tissue specimens (6 tissue specimens/dish) were arranged on a triangular grid placed on an inner dish with the epidermis upside. A liquid medium (Dulbecco's Modified Eagle Medium (DMEM), 0.7 ml) was added into the inner dish to conduct culture at 31° C. for 24 hours in a gas phase of 60% $O_2$ and 5% $CO_2$. The thus-obtained culture supernatant was used for the measurement of elastase activity.

The measurement of elastase activity was conducted in accordance with the method by Bieth et al. [Biochem. Biophys. Res. Commun., 53, 383–390 (1973)]. More specifically, a 20 mM solution of N-succinyl-$(Ala)_3$-p-nitroanilide was used as a substrate and added in a proportion of 5 µl per 95 µl of the culture supernatant. A reaction was conducted at 37° C. for 4 hours, and an absorbance at 410 nm was measured, thereby determining the amount of nitroaniline formed by the reaction with the enzyme. With respect to the enzyme activity, the activity that 1 nmol per hour of nitroaniline is formed was regarded as 1 unit.

As apparent from the result shown in FIG. 1, the rise and fall of the activity of an elastase in the cutaneous tissue released in the culture supernatant very much corresponded to the hair cycle thereof. More specifically, a high value was exhibited in a hair follicle-forming phase (growth phase), and a fall in activity value was recognized in a transient phase or resting phase. This result suggests that a rise in the activity of the elastase in the cutaneous tissue is indispensable to hair follicle formation and its growth.

TEST EXAMPLE 1

Elastase Activity-inhibiting Test in Cultured Human Fibroblast

Normal human fibroblasts commercially available from Dainippon Pharmaceutical Co., Ltd. were subcultured in a DMEM containing a 10% fetal bovine serum and used in this test. The cells separated from a Petri dish with a rubber policeman were suspended in physiological saline, collected by means of a low-speed centrifugal separator and washed 3 times with physiological saline. The thus-treated cells were suspended in a 0.1% Triton X-100/0.2 M Tris-HCl buffer (pH: 8.0) and ultrasonically disrupted to use as an enzyme solution.

125 mM N-Succinyl-$(Ala)_3$-p-nitroanilide was used as a substrate for the measurement of enzyme activity, and each subject (1 µl; its concentration is shown in Table 1) was added to the enzyme solution (100 µl) to conduct a reaction at 37° C. for 1 hour. The reaction was stopped by adding acetic acid (5 µl). The amount of nitroaniline formed was determined by measuring an absorbance at 405 nm by means of a spectrophotometer. Percent inhibition of elastase activity by the subject is shown in Table 1.

TABLE 1

| Subject | Concentration | Percent inhibition of elastase activity (%) |
|---|---|---|
| Compound 1 | 0.1 mM | 85.6 |
| Compound 2 | 0.1 mM | 82.1 |
| Compound 3 | 0.1 mM | 90.2 |
| Compound 4 | 1 mM | 68.4 |
| Compound 5 | 0.1 mM | 90.1 |
| Compound 6 | 0.1 mM | 88.7 |
| Compound 7 | 0.1 mM | 85.4 |
| Compound 8 | 0.1 mM | 89.6 |

Compound 1:

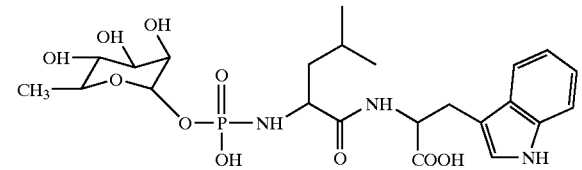

Compound 2:

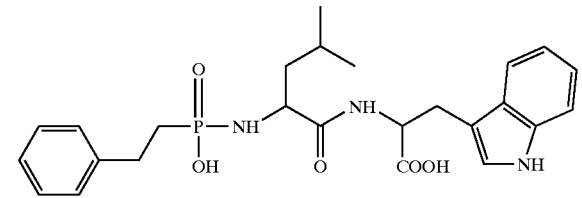

Compound 3:

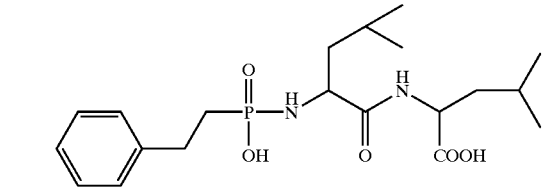

Compound 4:

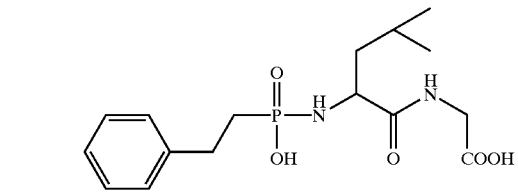

TABLE 1-continued

| Subject | Concentration | Percent inhibition of elastase activity (%) |
|---|---|---|

Compound 5:

[Chemical structure: KO-P(=O)(CK)-NH-CH(CH2CH(CH3)2)-C(=O)-NH-CH(CCCK)-CH2CH(CH3)2]

Compound 6:

[Chemical structure: KO-P(=O)(CK)-NH-CH(CH2CH(CH3)2)-C(=O)-NH-CH(CCCK)-CH2-indole]

Compound 7:

[Chemical structure: HS-CH2-CH(CH2Ph)-C(=O)-NH-CH2CH2-COOH]

Compound 8:

[Chemical structure: HS-CH2-CH(CH2Ph)-C(=O)-NH-CH2-COOH]

TEST EXAMPLE 2

Neutral Endopeptidase Activity-inhibiting Test in Cultured Human Fibroblast

Normal human fibroblasts commercially available from Dainippon Pharmaceutical Co., Ltd. were subcultured in a DMEM containing a 10% fetal bovine serum and used in this test. The cells separated from a Petri dish with a rubber policeman were suspended in phosphate-buffered physiological saline, collected by means of a low-speed centrifugal separator and washed 3 times with phosphate-buffered physiological saline. The thus-treated cells were suspended in a 0.1% Triton X-100/0.2 M Tris-HCl buffer (pH: 8.0) and ultrasonically disrupted to use as an enzyme solution.

The enzyme solution (2 μl), a solution (1 μl) of each subject compound and 20 mM glutaryl-Ala-Ala-Phe-4-methoxy-2-naphthylamine as a substrate for the measurement of enzyme activity were added to 100 μl of an MES buffer solution (100 mM, pH: 6.5), to which sodium chloride (300 mM) had been added, to conduct a reaction at 37° C. for 1 hour. The reaction was stopped by adding phosphoramidone so as to give a final concentration of 0.4 μM. Aminopeptidase M was added to the reaction mixture so as to give a final concentration of 20 mU, thereby conducting a reaction at 37° C. for 15 minutes. The amount of 4-methoxy-2-naphthylamine formed was determined by measuring a fluorescence intensity at an excitation wavelength of 340 nm and a fluorescence wavelength of 425 nm by means of a fluorescence spectrophotometer, thereby finding percent inhibition of neutral endopeptidase activity by the subject compound. The percent inhibition of neutral endopeptidase activity by the subject is shown in Table 2.

TABLE 2

| Subject | Concentration | Percent inhibition of neutral endopeptidase activity (%) |
|---|---|---|
| Compound 1 | 10 μM | 99.0 |
| Compound 2 | 10 μM | 98.8 |
| Compound 7 | 10 μM | 97.1 |
| Compound 8 | 10 μM | 96.3 |

TEST EXAMPLE 3

Test of Inhibiting Regeneration of Mouse Back Hair

Back hair of a group of 5 C3H mice aged 6 weeks was shaved over 2×4 cm by means of an electric hair clipper and an electric shaver so as not to damage their skins. Each subject was applied to the shaved sites twice a day in an amount of 100 μl/time over 4 weeks. The subject was dissolved in a solvent (80% ethanol) to prepare a solution of a concentration shown in the following Table 3. Only the solvent was applied to a control group. After 3 weeks, a photograph of each shaved site was taken at a fixed magnification for observing the state of regenerated hair to compare a regenerated hair area ratio (regenerated hair area/shaved area) of the test group with that of the control group. The results are shown in Table 3.

TABLE 3

| Subject | Concentration | Percent inhibition of hair growth after 3 weeks from shaving (%) |
|---|---|---|
| Compound 1 | 1 mM | 58.7 |
| Compound 2 | 1 mM | 59.1 |
| Compound 3 | 1 mM | 64.8 |
| Compound 4 | 10 mM | 60.5 |
| Compound 5 | 1 mM | 74.2 |
| Compound 6 | 1 mM | 62.1 |
| Compound 7 | 1 mM | 59.7 |
| Compound 8 | 1 mM | 71.6 |

As apparent from Tables 1 to 3, the subjects, which are elastase inhibitors or neutral endopeptidase inhibitors, had an excellent inhibitory effect on hair growth.

EXAMPLE 2

Hair Growth Inhibiting Lotion

|   |   | (wt. %) |
|---|---|---|
| A | Polyoxyethylene hardened castor oil | 0.8 |
|   | Ethanol | 30.0 |
| B | Compound 2 | 1.0 |
|   | Sodium dodecylsulfate | 0.12 |
|   | Dodecylmethylamine oxide | 0.18 |

-continued

|   | (wt. %) |
|---|---|
| Isopropyl alcohol | 15.0 |
| Benzyl alcohol | 15.0 |
| Glycerol | 2.0 |
| Purified water | Balance |

The components belonging to A were dissolved, and the components belonging to B were separately dissolved. The solution of B was added to the solution of A to uniformly stir and mix both solutions, thereby obtaining a hair growth inhibiting lotion.

EXAMPLE 3

Hair Growth Inhibiting Cream

|   |   | (wt. %) |
|---|---|---|
| A | Liquid paraffin | 10.0 |
|   | Squalane | 7.0 |
|   | Jojoba oil | 3.0 |
|   | Solid paraffin | 3.0 |
|   | Polyoxyethylene cetyl ether | 2.0 |
|   | Sorbitan sesquioleate | 1.0 |
|   | Potassium hydroxide | 0.1 |
| B | Compound 7 | 1.0 |
|   | Glycerol | 3.0 |
|   | Ethylparaben | 0.1 |
|   | Purified water | Balance |

The components belonging to A were heated to melt them, and the components belonging to B were separately heated to melt them. The melt of B was added to the melt of A to uniformly stir and mix both melts, thereby emulsifying them. The resultant emulsion was then cooled to obtain a hair growth inhibiting cream.

EXAMPLE 4

Hair Growth Inhibiting Foam

|   |   | (wt. %) |
|---|---|---|
| A | Compound 8 | 1.0 |
|   | Cetanol | 0.1 |
|   | Propylene glycol | 2.0 |
|   | Dimethyl silicone oil | 2.0 |
|   | Polyoxyethylene hardened castor oil | 2.5 |
|   | Liquid paraffin | 1.0 |
|   | Polyvinyl pyrrolidone | 0.5 |
|   | Methylparaben | 0.2 |
|   | Ethanol | 10.0 |
|   | Purified water | Balance |
| B | Liquefied petroleum gas (propellant) | 4.0 |

The components belonging to A were uniformly mixed and placed in a container. The component of B was charged into the container in accordance with a method known per se in the art to obtain a hair growth inhibiting foam.

EXAMPLE 5

Aerosol

|   |   | (wt. %) |
|---|---|---|
| A | Compound 1 | 1.0 |
|   | Cetanol | 1.2 |
|   | Propylene glycol | 4.0 |
|   | Ethanol | 8.0 |
|   | Purified water | Balance |
| B | Liquefied petroleum gas (propellant) | 4.0 |

The components belonging to A were uniformly mixed and placed in a container. The component of B was charged into the container in accordance with a method known per se in the art to obtain an aerosol.

Japanese Patent Application No. 10-005959, filed on Jan. 14, 1998, is incorporated herein by reference in its entirety.

What is claimed is:

1. A method of inhibiting hair growth, which comprises topically administering to an affected area of a subject in need thereof an inhibitor of elastase-like enzymes, wherein said inhibitor of elastase-like enzymes is not a matrix metalloproteinase inhibitor, and wherein said inhibitor of elastase-like enzymes is not a mercaptopropionamide compound.

2. The method according to claim 1, wherein the inhibitor of elastase-like enzymes is an inhibitor of an elastase-like enzyme derived from a dermoepidermal fibroblast.

3. The method according to claim 1, wherein said subject is a human.

4. The method according to claim 1, wherein said inhibitor of elastase-like enzymes is a phosphonic acid compound, or a derivative or salt thereof.

* * * * *